(12) United States Patent
Wagle et al.

(10) Patent No.: US 6,458,819 B1
(45) Date of Patent: Oct. 1, 2002

(54) THIAZOLIUM COMPOUNDS AND TREATMENTS OF DISORDERS ASSOCIATED WITH PROTEIN AGING

(75) Inventors: Dilip Wagle; Sarah Vasan; Jack Egan, all of New York, NY (US)

(73) Assignee: Alteon, Inc., Ramsey, NJ (US)

( * ) Notice: Subject to any disclaimer, the term of this patent is extended or adjusted under 35 U.S.C. 154(b) by 0 days.

(21) Appl. No.: 09/792,422

(22) Filed: Feb. 23, 2001

Related U.S. Application Data

(60) Provisional application No. 60/184,266, filed on Feb. 23, 2000.

(51) Int. Cl.$^7$ ............................................. A61K 31/427
(52) U.S. Cl. ...................................... 514/365; 514/367
(58) Field of Search ................................. 514/365, 367

(56) References Cited

U.S. PATENT DOCUMENTS 5,580,904 A * 12/1996 Ishikura et al.
5,656,261 A * 8/1997 Cerami et al.
5,853,703 A * 12/1998 Cerami et al.
6,007,865 A * 12/1999 Cerami et al.
6,121,300 A * 9/2000 Wagle et al.

FOREIGN PATENT DOCUMENTS

WO          WO99/48470      * 9/1999

* cited by examiner

*Primary Examiner*—William R. A. Jarvis
*Assistant Examiner*—Vickie Kim
(74) *Attorney, Agent, or Firm*—Dechert

(57) ABSTRACT

A method and compositions are disclosed for, among other things, in an animal, (i) improving the elasticity or reducing wrinkles of the skin, treating (ii) diabetes or treating or preventing (iii) adverse sequelae of diabetes, (iv) kidney damage, (v) damage to blood vasculature, (vi) hypertension, (vii) retinopathy, (viii) damage to lens proteins, (ix) cataracts, (x) peripheral neuropathy, or (xi) osteoarthritis.

5 Claims, No Drawings

THIAZOLIUM COMPOUNDS AND TREATMENTS OF DISORDERS ASSOCIATED WITH PROTEIN AGING

This application claims the priority of U.S. Provisional Application No. 60/184,266 filed Feb. 23, 2000.

The present invention relates, among other things, to thiazole compounds and, in an animal, (i) improving the elasticity or reducing wrinkles of the skin, treating (ii) diabetes or treating or preventing (iii) adverse sequelae of diabetes, (iv) kidney damage, (v) damage to blood vasculature, (vi) hypertension, (vii) retinopathy, (viii) damage to lens proteins, (ix) cataracts, (x) peripheral neuropathy, or (xi) osteoarthritis.

The reaction between glucose and proteins has been known for some time. Maillard in 1912, observed that glucose or other reducing sugars react with amino acids to form adducts that undergo a series of dehydrations and rearrangements to form stable brown pigments. Further studies have suggested that stored and heat treated foods undergo nonenzymatic browning as a result of the reaction between glucose and polypeptides, resulting in cross-links and decreased bioavailability.

This reaction between reducing sugars and food proteins was found to have its parallel in vivo. Nonenzymatic reaction between glucose and the free amino groups on proteins to form a stable, 1-deoxyketosyl adduct, known as the Amadori product, has been shown to occur with hemoglobin, where a reaction of the amino terminal of the beta-chain of hemoglobin with glucose forms the adduct known as hemoglobin A1c. Like reactions have been found to occur with a variety of other body proteins, such as lens crystallins, collagen and nerve proteins. See Bucala et al., "Advanced Glycosylation; Chemistry, Biology, and Implications for Diabetes and Aging" in Advances in Pharmacology, Vol. 23, pp. 1–34, Academic Press (1992).

Brown pigments with spectral and fluorescent properties similar to those of late-stage Maillard products have also been observed in vivo in association with several long-lived proteins, such as lens proteins and collagen from aged individuals. An age-related linear increase in pigment has been observed in human dura collagen between the ages of 20 to 90 years. Interestingly, the aging of collagen can be mimicked in vitro by cross-linking induced by glucose. Glucose-induced collagen products capture of other proteins, which capture is theorized to occur by a crosslinking reaction, and is believed to account for the observed accumulation of albumin and antibodies in kidney basement membrane. These reaction products with glucose are typically referred to as "advanced glycosylation endproducts" or AGEs.

Reagents have been identified that inhibit the formation of advanced glycosylation endproducts. These are believed to operate by reacting with an early glycosylation product. Some such reagents are believed to operate by breaking at least certain sugar-derived crosslinks. One of the agents identified as an inhibitor was aminoguanidine, and further testing has borne out its efficacy.

While the success that has been achieved with aminoguanidine and other compounds is promising, a need continues to exist to identify and develop additional inhibitors that broaden the availability and perhaps the scope of this potential activity and its diagnostic and therapeutic utility.

SUMMARY OF THE INVENTION

In accordance with the present invention, a method and compositions are disclosed for, among other things, in an animal, (i) improving the elasticity or reducing wrinkles of the skin, treating (ii) diabetes or treating or preventing (iii) adverse sequelae of diabetes, (iv) kidney damage, (v) damage to blood vasculature, (vi) hypertension, (vii) retinopathy, (viii) damage to lens proteins, (ix) cataracts, (x) peripheral neuropathy, or (xi) osteoarthritis. Without being bound by theory, these effects are believed to be related to the inhibition of formation of advanced glycosylation of proteins (protein aging) and to breaking the cross-links that form between advanced glycosylation (glycation) endproducts (AGEs) or between AGEs and other proteins. The invention further relates to preventing or reversing advanced glycosylation endproducts and cross-linking caused by other reactive sugars present in vivo or in foodstuffs, including ribose, galactose and fructose.

In particular, the compositions comprise agents for inhibiting the formation of and reversing the pre-formed advanced glycosylation (glycation) endproducts and breaking the subsequent cross-links. While not wishing to be bound by any theory, it is believed that the breaking of the pre-formed advanced glycosylation (glycation) endproducts and cross-links is a result of the cleavage of alpha-dicarbonyl-based protein crosslinks present in the advanced glycosylation endproducts.

Certain of the agents useful in the present invention are members of the class of compounds known as thiazoles.

The compounds, and their compositions, utilized in this invention are believed to react with an early glycosylation product thereby preventing the same from later forming the advanced glycosylation end products that lead to cross-links, and thereby, to molecular or protein aging and other adverse molecular consequences. Additionally, they react with already formed advanced glycosylation end products to reduce the amount of such products.

The ability to inhibit the formation of advanced glycosylation endproducts, and to reverse the already formed advanced glycosylation products in the body carries with it significant implications in all applications where advanced glycation and concomitant molecular crosslinking is a serious detriment. Thus, in the area of food technology, for instance, the retardation of food spoilage would confer an obvious economic and social benefit by making certain foods of marginal stability less perishable and therefore more available for consumers. Spoilage would be reduced, as would the expense of inspection, removal, and replacement, and the extended availability of the foods could aid in stabilizing their price in the marketplace. Similarly, in other industrial applications where the perishability of proteins is a problem, the admixture of the agents of the present invention in compositions containing such proteins would facilitate the extended useful life of the same. Presently used food preservatives and discoloration preventatives such as sulfur dioxide, known to cause toxicity including allergy and asthma in animals, can be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as a consequence of diabetes. Accordingly, the ability to either retard or substantially inhibit the formation of advanced glycosylation endproducts, and to reduce the amount of cross-links formed between advanced glycosylation endproducts and other proteins in the body carries the promise for treatment of the complications of diabetes and aging for instance, and thereby improving the quality and, perhaps, duration of animal and human life.

The present agents are also useful in the area of personal appearance and hygiene, as they prevent, and reverse, the staining of teeth by cationic anti-microbial agents with anti-plaque properties, such as chlorhexidine.

DETAILED DESCRIPTION

Provided is, among other things, a method of, in an animal, (i) improving the elasticity or reducing wrinkles of the skin, treating (ii) diabetes or treating or preventing (iii) adverse sequelae of diabetes, (iv) kidney damage, (v) damage to blood vasculature, (vi) hypertension, (vii) retinopathy, (viii) damage to lens proteins, (ix) cataracts, (x) peripheral neuropathy, or (xi) osteoarthritis, the method comprising administering an amount effective therefor of one or more compounds of the following formula:

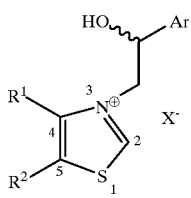

I wherein
  $R^1$ and $R^2$ are independently hydrogen, hydroxy(lower) alkyl, lower acyloxy(lower)alkyl, or lower alkyl, or $R^1$ and $R_2$ together with their ring carbons form an aromatic fused ring;
  Ar is an aryl group;
  X is a pharmaceutically acceptable anion,
wherein each said fused aromatic ring or aryl group can be substituted with hydroxy groups and up to two groups selected from halo, loweralkoxy or di(loweralkyl)amino groups, or one or more alkyl, carboxy, carboxyalkyl, nitro or alkylenedioxy groups.

In some embodiments, the invention relates to a pharmaceutical composition for administration to an animal for (i) improving the elasticity or reducing wrinkles of the skin, treating (ii) diabetes or treating or preventing (iii) adverse sequelae of diabetes, (iv) kidney damage, (v) damage to blood vasculature, (vi) hypertension, (vii) retinopathy, (viii) damage to lens proteins, (ix) cataracts, (x) peripheral neuropathy, or (xi) osteoarthritis, the composition comprising one or more compounds of the following formula:

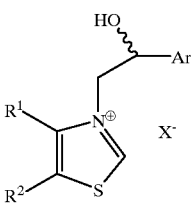

I wherein $R^1$ and $R^2$ are independently hydrogen, hydroxy (lower) alkyl, lower acyloxy(lower)alkyl, or lower alkyl, or $R_1$ and $R_2$ together with their ring carbons form an aromatic fused ring;
  Ar is an aryl group;
  X is a pharmaceutically acceptable anion,
wherein said fused aromatic rings or aryl group can be substituted with up to two groups selected from halo, hydroxy, loweralkoxy or di(loweralkyl)amino groups, or one or more alkyl, carboxy, carboxyalkyl, nitro or alkylenedioxy groups.

In some embodiments, the invention relates to a method of, in an animal, (i) improving the elasticity or reducing wrinkles of the skin, treating (ii) diabetes or treating or preventing (iii) adverse sequelae of diabetes, (iv) kidney damage, (v) damage to blood vasculature, (vi) hypertension, (vii) retinopathy, (viii) damage to lens proteins, (ix) cataracts, (x) peripheral neuropathy, or (xi) osteoarthritis, the method comprising administering an amount effective therefor of one or more compounds of the following formula:

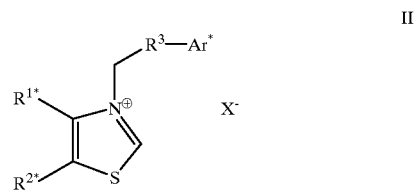

II wherein $R^{1*}$ and $R^{2*}$ are independently selected from the group consisting of hydroxymethyl and methyl;
  $R^3$ is carbonyl or hydroxymethylene;
  Ar* is phenyl optionally substituted with one to two groups which are halo, hydroxy, lower alkoxy, alkylenedioxy or di(lower)alkylamino group; and
  X is a pharmaceutically acceptable anion;
wherein the compound is substituted with at least one hydroxy group incorporated into $R^{1*}$, $R^{2*}$, $R^3$ or Ar*.

Lower alkyl groups contain 1–6 carbon atoms and include methyl, ethyl, propyl, butyl, pentyl, hexyl, and the corresponding branched-chain isomers thereof. Lower alkenyl or alkynyl groups contain from 2 to 6 carbon atoms. Similarly, the lower alkoxy groups contain from 1 to 6 carbon atoms, and include methoxy, ethoxy, propoxy, butoxy, pentoxy, and hexoxy, and the corresponding branched-chain isomers thereof. These groups are optionally substituted by one or more halo, hydroxy, amino or lower alkylamino groups.

Lower alkanoly(lower)alkyl groups contain from 2 to 6 carbon atoms. Typical alkanoyl groups are those such as acetoxy or ethanoyloxy, propanoyloxy, butanoyloxy, pentanoyloxy, hexanoyloxy, and the corresponding branched chain isomers thereof.

The aryl groups are those containing 6–10 carbon atoms, such as naphthyl, phenyl and lower alkyl substituted-phenyl, e.g., tolyl and xylyl, and are optionally substituted by one to two halo, hydroxy, lower alkoxy or di(lower)alkylamino groups. Preferred aryl groups are phenyl, methoxyphenyl and 4-bromophenyl groups.

The halo atoms can be fluoro, chloro, bromo or iodo.

For the purposes of this invention, the compounds of formula (I) are formed as biologically or pharmaceutically acceptable salts. Useful salt forms are the halides, particularly the bromide and chloride, tosylate, methanesulfonate, and mesitylenesulfonate salts. Other related salts can be formed using similarly non-toxic, and biologically and pharmaceutically acceptable anions.

Exemplary compounds of the invention include:
3-(2-Phenyl-2-hydroxyethyl)-4,5-dimethylthiazolium,
S(–) 3-(2-Phenyl-2-hydroxyethyl)-4,5-dimethylthiazolium,
R(–) 3-(2-Phenyl-2-hydroxyethyl)-4,5-dimethylthiazolium,
3-[2-(2'-Hydroxyphenyl)-2-oxoethyl]-4,5-dimethylthiazolium, 3-[2-(3'-Hydroxyphenyl)-2-oxoethyl]-4,5-dimethylthiazolium,
3-[2-(4'-Hydroxyphenyl)-2-oxoethyl]-4,5-dimethylthiazolium,
3-(2-phenyl-2-oxoethyl)-4-methyl-5-(hydroxymethyl)-thiazolium,
3-(2-phenyl-2-oxoethyl)-4-(hydroxymethyl)-5-methylthiazolium,
3-(2-phenyl-2-oxoethyl)-4,5-(dihydroxymethyl)-thiazolium,
3-[2-(2', 4'-dihydroxyphenyl)-2-oxoethyl]-4,5-dimethylthiazolium,
3-[2-(3', 5'-dihydroxyphenyl)-2-oxoethyl]-4,5-dimethylthiazolium,
3-[2-(2', 5'-dihydroxyphenyl)-2-oxoethyl]-4,5-dimethylthiazolium,
3-[2-(2', 6'-dihydroxyphenyl)-2-oxoethyl]-4,5-dimethylthiazolium,
3-[2-(3', 4'-dihydroxyphenyl)-2-oxoethyl]-4,5-dimethylthiazolium and
3-[2-(2', 3'-dihydroxyphenyl)-2-oxoethyl]-4,5-dimethylthiazolium compounds and salts thereof.

The above compounds are capable of inhibiting the formation of advanced glycosylation endproducts on target molecules, including, for instance, proteins, as well as being capable of breaking or reversing already formed advanced glycosylation endproducts on such proteins. The cross-linking of protein by formation of advanced glycosylation endproducts contributes to the entrapment of other proteins and results in the development in vivo of conditions such as reduced elasticity and wrinkling of the skin, certain kidney diseases, atherosclerosis, osteoarthritis and the like. Similarly, plant material that undergoes nonenzymatic browning deteriorates and, in the case of foodstuffs, becomes spoiled or toughened and, consequently, inedible, unpalatable or non-nutritious. Thus, the compounds employed in accordance with this invention inhibit this late-stage Maillard effect and intervene in the deleterious changes described above, and reduce the level of the advanced glycosylation endproducts already present in the protein material.

The rationale of the present invention is to use agents which block, as well as reverse, the post-glycosylation step, e.g., the formation of fluorescent chromophores and cross-links, the presence of which is associated with, and leads to adverse sequelae of diabetes and aging. An ideal agent would prevent the formation of such chromophores and of cross-links between protein strands and trapping of proteins onto other proteins, such as occurs in arteries and in the kidney, and reverse the level of such cross-link formation already present.

The chemical nature of the early glycosylation products with which the compounds of the present invention are believed to react can vary. Accordingly the term "early glycosylation product(s)" as used herein is intended to include any and all such variations within its scope. For example, early glycosylation products with carbonyl moieties that are involved in the formation of advanced glycosylation endproducts, and that can be blocked by reaction with the compounds of the present invention, have been postulated. In one embodiment, the early glycosylation product can comprise the reactive carbonyl moieties of Amadori products or their further condensation, dehydration and/or rearrangement products, which can condense to form advanced glycosylation endproducts. In another scenario, reactive carbonyl compounds, containing one or more carbonyl moieties (such as glycolaldehyde, glyceraldehyde or 3-deoxyglucosone) can form from the cleavage of Amadori or other early glycosylation endproducts, and by subsequent reactions with an amine or Amadori product, can form carbonyl containing advanced glycosylation products such as alkylformyl-glycosylpyrroles.

Several investigators have studied the mechanism of advanced glycosylation product formation. In vitro studies by Eble et al., (1983), "Nonenzymatic Glucosylation and Glucose-dependent Cross-linking of Protein", J. Biol. Chem., 258:9406–9412, concerned the cross-linking of glycosylated protein with nonglycosylated protein in the absence of glucose. Eble et al. sought to elucidate the mechanism of the Maillard reaction and accordingly conducted controlled initial glycosylation of RNase as a model system. In one aspect, the glycosylated protein material was isolated and placed in a glucose-free environment and observed to determine the extent of cross-linking. Eble et al. observed that cross-linking continued to occur not only with the glycosylated protein but with non-glycosylated proteins as well. One of the observations was that the reaction between glycosylated protein and the protein material appeared to occur at the location on the amino acid side-chain of the protein. Confirmatory experimentation demonstrated that free lysine competed with the lysine on RNase for the binding of glycosylated protein.

While not wishing to be bound by any particular theory as to the mechanism by which the compounds of the instant invention reverse already formed advanced glycosylation endproducts, studies have been structured to elucidate a possible mechanism. Earlier studies examining the fate of the Amadori product (AP) in vivo have identified one likely route that could lead to the formation of covalent, glucose-derived protein crosslinks. This pathway proceeds by dehydration of the AP via successive beta-eliminations as shown in the Scheme A of U.S. Pat. No. 5,853,703. Thus, loss of the 4-hydroxyl of the AP (1) gives a 1,4-dideoxy-1-alkylamino-2,3-hexodiulose (AP-dione) (2). An AP-dione with the structure of an amino-1,4-dideoxyosone has been isolated by trapping model APs with the AGE-inhibitor aminoguanidine. Subsequent elimination of the 5-hydroxyl gives a 1,4,5-trideoxy-1-alkylamino-2,3-hexulos-4-ene (AP-ene-dione) (3), which has been isolated as a triacetyl derivative of its 1,2-enol form. Amadori-diones, particularly the AP-ene-dione, would be expected to be highly reactive toward protein crosslinking reactions by serving as targets for the addition of the amine (Lys, His)-, or sulfhydryl (Cys)-based nucleophiles that exist in proteins, thereby producing stable crosslinks of the form (4).

Note that the linear AP-ene-dione of (3) and the stable cross-link of (4) can cyclize to form either 5- or 6-member lactol rings. See, the scheme shown in U.S. Pat. No. 5,853,703.

The possibility that a major pathway of glucose-derived crosslink formation proceeds through an AP-ene-dione intermediate was investigated by experiments designed to test the occurrence of this pathway in vivo as well as to effect the specific cleavage of the resultant α-dicarbonyl-based protein crosslinks. Without being limited to theory, the thiazole compounds of the invention are believed to act as "bidentate" nucleophiles, particularly designed to effect a carbon—carbon breaking reaction between the two carbonyls of the crosslink, in a similar manner to Scheme B of U.S. Pat. No. 5,853,703.

The present invention likewise relates to methods for inhibiting the formation of advanced glycosylation endproducts, and reversing the level of already formed advanced glycosylation endproducts, which comprise contacting the target molecules with a composition of the present invention. In the instance where the target proteins are contained in foodstuffs, whether of plant or animal origin, these foodstuffs could have applied to them by various conventional means a composition containing the present agents.

In the food industry, sulfites were found years ago to inhibit the Maillard reaction and are commonly used in processed and stored foods. Recently, however, sulfites in food have been implicated in severe and even fatal reactions in asthmatics. As a consequence, the sulfite treatment of fresh fruits and vegetables has been banned. The mechanism for the allergic reaction is not known. Accordingly, the present compositions and agents offer a nontoxic alternative to sulfites in the treatment of foods in this manner.

The present methods and compositions hold the promise for arresting, and to some extent reversing, the aging of key proteins both in animals and plants, and concomitantly, conferring both economic and medical benefits as a result thereof. In the instance of foodstuffs, the administration of the present composition holds the promise for retarding food spoilage thereby making foodstuffs of increased shelf life and greater availability to consumers. Replacement of currently-used preservatives, such as sulfur dioxide known to cause allergies and asthma in humans, with nontoxic, biocompatible compounds is a further advantage of the present invention.

The therapeutic implications of the present invention relate to the arrest, and to some extent, the reversal of the aging process which has, as indicated earlier, been identified and exemplified in the aging of key proteins by advanced glycosylation and cross-linking. Thus, body proteins, and particularly structural body proteins, such as collagen, elastin, lens proteins, nerve proteins, kidney glomerular basement membranes and other extravascular matrix components would all benefit in their longevity and operation from the practice of the present invention. The present invention thus reduces the incidence of pathologies involving the entrapment of proteins by cross-linked target proteins, such as retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, and other conditions. Likewise, all of these conditions are in evidence and tend to occur at an accelerated rate in patients afflicted with diabetes mellitus as a consequence of this hyperglycemia. Thus, the present therapeutic method is relevant to treatment of these and related conditions in patients either of advanced age or those suffering from one of the mentioned pathologies.

Protein cross-linking through advanced glycosylation product formation can decrease solubility of structural proteins such as collagen in vessel walls and can also trap serum proteins, such as lipoproteins to the collagen. Also, this can result in increased permeability of the endothelium and consequently covalent trapping of extravasated plasma proteins in subendothelial matrix, and reduction in susceptibility of both plasma and matrix proteins to physiologic degradation by enzymes. For these reasons, the progressive occlusion of diabetic vessels induced by chronic hyperglycemia is believed to result from excessive formation of glucose-derived cross-links. Such diabetic microvascular changes and microvascular occlusion can be effectively prevented and reversed by chemical inhibition and reversal of the advanced glycosylation product formation utilizing a composition and the methods of the present invention.

Molecular cross-linking through advanced glycosylation product formation can decrease solubility of structural proteins such as collagen in vessel walls and can also trap serum proteins, such as lipoproteins to the collagen. Also, this can result in increased permeability of the endothelium and consequently covalent trapping of extravasated plasma proteins in subendothelial matrix, and reduction in susceptibility of both plasma and matrix proteins to physiologic degradation by enzymes. For these reasons, the progressive occlusion of diabetic vessels induced by chronic hyperglycemia has been hypothesized to result from excessive formation of sugar-derived and particularly, glucose-derived cross-links. Such diabetic microvascular changes and microvascular occlusion can be effectively prevented and reversed by chemical inhibition and reversal of the advanced glycosylation product formation utilizing a composition and the methods of the present invention.

Studies indicate that the development of chronic diabetic damage in target organs is primarily linked to hyperglycemia so that tight metabolic control would delay or even prevent end-organ damage. See Nicholls et al., Lab. Invest., 60, No. 4, p. 486 (1989), which discusses the effects of islet isografting and aminoguanidine in murine diabetic nephropathy. These studies further evidence that aminoguanidine diminishes aortic wall protein cross-linking in diabetic rats and confirm earlier studies by Brownlee et al., Science, 232:1629–1632 (1986) to this additional target organ of complication of diabetes. Also, an additional study showed the reduction of immunoglobulin trapping in the kidney by aminoguanidine (Brownlee et al., Diabetes, (1):42A(1986)).

Further evidence in the streptozotocin-diabetic rat model that aminoguanidine administration intervenes in the development of diabetic nephropathy was presented by Brownlee et ale, Science, 232:1629–1632 (1986), with regard to morphologic changes in the kidney which are hallmarks of diabetic renal disease. These investigators reported that the increased glomerular basement membrane thickness, a major structural abnormality characteristic of diabetic renal disease, was prevented with aminoguanidine.

Taken together, these data strongly suggest that inhibition and reversal of the formation of advanced glycosylation endproducts (AGEs), by the teaching of the present invention, can prevent, as well as to some extent reverse late, as well as early, structural lesions due to diabetes, as well as changes during aging caused by the formation of AGEs.

Diabetes-induced changes in the deformability of red blood cells, leading to more rigid cell membranes, is another manifestation of cross-linking and aminoguanidine has been shown to prevent it in vivo. In such studies, New Zealand White rabbits, with induced, long-term diabetes are used to study the effects of a test compound on red blood cell (RBC) deformability. The test compound is administered at a rate of 100 mg/kg by oral gavage (tube delivery to stomach) to diabetic rabbits.

A further consequence of diabetes is the hyperglycemia-induced matrix bone differentiation resulting in decreased bone formation usually associated with chronic diabetes. In animal models, diabetes reduces matrix-induced bone differentiation by 70%.

In the instance where the compositions of the present invention are utilized for in vivo or therapeutic purposes, it can be noted that the compounds or agents used therein are biocompatible. Pharmaceutical compositions can be prepared with a therapeutically effective quantity of the agents or compounds of the present invention and can include a pharmaceutically acceptable carrier, selected from known materials utilized for this purpose. Such compositions can be prepared in a variety of forms, depending on the method of administration. Also, various pharmaceutically acceptable addition salts of the compounds of the invention can be utilized.

A liquid form would be utilized in the instance where administration is by intravenous, intramuscular or intraperitoneal injection. When appropriate, solid dosage forms such as tablets, capsules, or liquid dosage formulations such as solutions and suspensions, etc., can be prepared for oral administration. For topical or dermal application to the skin or eye, a solution, a lotion or ointment can be formulated with the agent in a suitable vehicle such as water, ethanol, propylene glycol, perhaps including a carrier to aid in penetration into the skin or eye. For example, a topical preparation could include up to about 10% of a compound of the invention. Other suitable forms for administration to other body tissues are also contemplated.

In the instance where the present method has therapeutic application, the animal host intended for treatment can have administered to it a quantity of one or more of the agents, in a suitable pharmaceutical form. Administration can be accomplished by known techniques, such as oral, topical and parenteral techniques such as intradermal, subcutaneous, intravenous or intraperitoneal injection, as well as by other conventional means. Administration of the agents can take place over an extended period of time at a dosage level of, for example, up to about 30 mg/kg. Preferably, the dosage level 20 mg/kg or less.

The invention also extends to a method of inhibiting and reversing the discoloration of teeth resulting from nonenzymatic browning in the oral cavity which comprises administration to a subject in need of such therapy an amount effective to inhibit and reverse the formation of advanced glycosylation endproducts of a composition comprising an agent of the invention.

The nonenzymatic browning reaction which occurs in the oral cavity results in the discoloration of teeth. Presently used anti-plaque agents accelerate this nonenzymatic browning reaction and further the staining of the teeth. Recently, a class of cationic anti-microbial agents with remarkable anti-plaque properties have been formulated in oral rinses for regular use to kill bacteria in the mouth. These agents, the cationic antiseptics, include such agents as alexidine, cetyl pyridinium chloride, chlorhexidine gluconate, hexetidine, and benzalkonium chloride.

Tooth staining by chlorhexidine and other anti-plaque agents apparently results from the enhancement of the Maillard reaction. Nordbo, J. Dent. Res., 58:1429 (1979) reported that chlorhexidine and benzalkonium chloride catalyze browning reactions in vitro. Chlorhexidine added to mixtures containing a sugar derivative and a source of amino groups underwent increased color formation, attributed to the Maillard reaction. It is also known that use of chlorhexidine results in an increased dental pellicle. Nordbo proposed that chlorhexidine resulted in tooth staining in two ways: first, by increasing formation of pellicle which contains more amino groups, and secondly, by catalysis of the Maillard reaction leading to colored products.

In accordance with this method, the compounds of the invention are formulated into compositions adapted for use in the oral cavity. Particularly suitable formulations are oral rinses and toothpastes incorporating the active agent.

In the practice of this invention, conventional formulating techniques are utilized with nontoxic, pharmaceutically acceptable carriers typically utilized in the amounts and combinations that are well-known for the formulation of such oral rinses and toothpastes.

The agents of the invention are formulated in compositions in an amount effective to inhibit and reverse the formation of advanced glycosylation endproducts. This amount will, of course, vary with the particular agent being utilized and the particular dosage form, but typically is in the range of 0.01% to 1.0%, by weight, of the particular formulation.

Certain of the compounds are conveniently prepared by chemical syntheses, well-known in the art. Certain of the compounds are well-known and readily available from chemical supply houses or can be prepared by synthetic methods specifically published therefor. In the nonlimiting exemplary synthetic schemes below, one skilled in the art will appreciate that while some product compounds are shown as specific optical isomers and others are shown as racemic compounds, the use of appropriate reaction conditions and reagents, well known in the art, to customize the degree of reaction stereoselectivity are within the scope of compounds of the invention. For example, compound 2 may be obtained as a racemic mixture from compound 1 or as an S (compoound 2a) or R stereoisomer depending on the reducing agent employed. Similarly, the chemical reagents shown in the schemes below provide nonlimiting examples of means well known in the art to carry out the reaction steps shown. Substitution of comparable reagents to achieve different stereoselectivity, even when not shown explicitly by the scheme, would be well known in the art at the time of filing. Moreover, synthetic processes and stereoselective purifications, such as chromatography on stereoselective media can be used to achieve 90%, 95%, 98%, 99% or better isomeric purity, such that compositions substantially free of the non-desired isomer can be prepared.

A first synthesis scheme for making the compounds of the invention, the hydroxyl is incorporated into a nucleophile used to derivatize a thiazole compound, as follows:

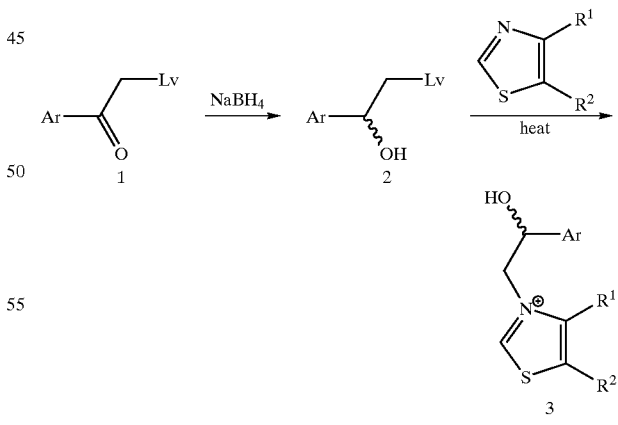

where Lv is a leaving group such as chloro. In a related synthesis, Compound 1 is reduced with a stereoselective reducing agent such as (−) DIP-chloride [(−)-B-chlorodiisopinocampheylborane] or (+) DIP-chloride [(+)-B-chlorodiisopinocampheylborane]. For example:

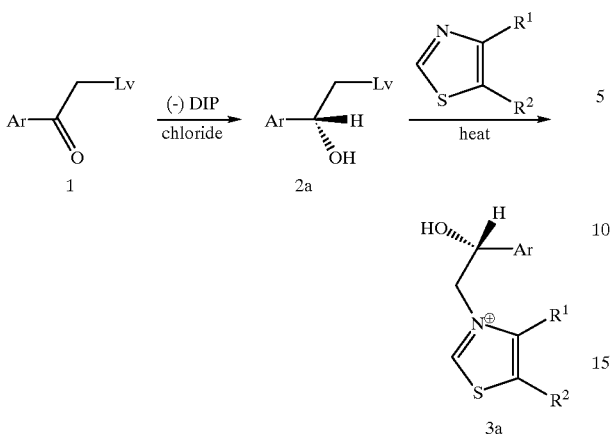

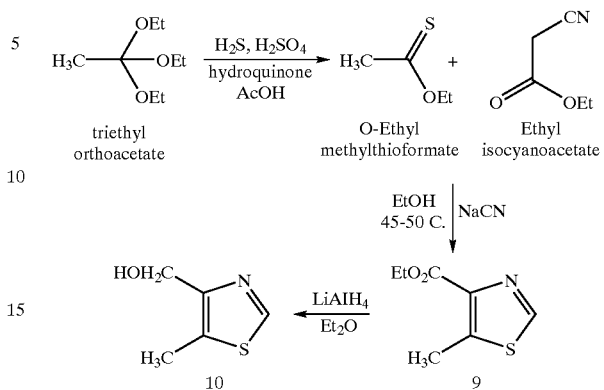

Substitution of (+) DIP-chloride results predominately in the mirror image to compound 3a.

In a second synthesis, acetyl benzene compounds that incorporate hydroxylations to the aromatic ring are derivatized to add a leaving group to the alpha methyl group, and the resulting intermediate is reacted with a thiazole compound, as exemplified below:

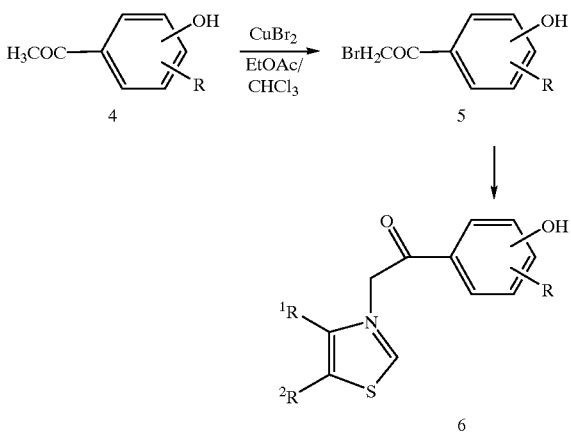

In a third synthesis, formamide is first converted to thioformamide by reaction with phosphorus pentasulfide. Thioformamide is reacted with ethyl 2-chloroacetoacetate in dry dioxane as follows:

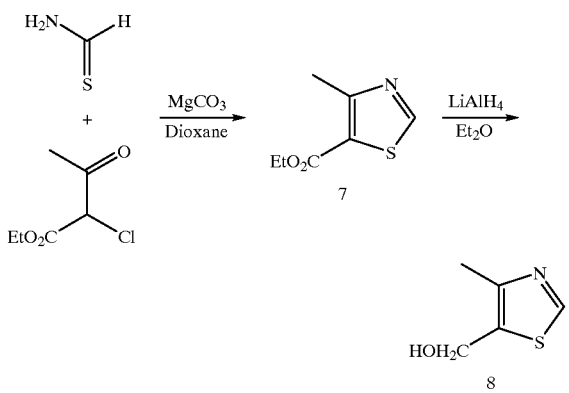

Compound 8 can then be reacted with a compound 1 or a compound 2 to make a compound of the invention.

The 4-position on the thiazole ring can be made into a hydroxymethyl group as shown below:

Compound 10 can then be reacted with a compound 1 or a compound 2 to make a compound of the invention.

Note that reaction conditions indicated in the various reaction schemes are exemplary: such conditions as solvent and temperature are subject to modification within ordinary skill.

Additional information on appropriate synthetic schemes can be found, for example, in U.S. Pat. No. 5,853,703.

EXAMPLE 1

3-(2-Phenyl-2-hydroxyethyl)-4,5-dimethyl-thiazolium chloride:

2-Chloro-1-phenylethanol:

2-Chloroacetophenone (5.0 g, 32 mmole) was dissolved in methanol (25 mL) and cooled to 0° C. Sodium borohydride (1.2 g, 32 mmole) was added and stirred at 0° C. for 30 minutes. The reaction mixture was neutralized by adding conc. HCl to pH 7.0 and evaporated to dryness. The residue was dissolved in ethanol (30 mL) and filtered, washed with ethanol. The ethanol was evaporated to dryness. The residue was dissolved in methylene chloride (20 mL) and dried over sodium sulfate. The methylene chloride solution was filtered and evaporated to give the desired product as an oil; yield 4.84 g (5.6%).

3-(2-Phenyl-2-hydroxyethyl)-4,5-dimethyl-thiazolium chloride:

The neat mixture of 2-chloro-1-phenylethanol (2.34 g, 14.9 mmole) and 4,5-dimethylthiazole (1.69 g, 14.9 mmole) were heated with stirring at 135° C. for 28 hrs. It was cooled to room temperature and water (30 mL) was added to the reaction mixture with stirring, and then was extracted with ether (30 mL). The water layer was treated with actived carbon and evaporated to dryness. It was crystallized from a mixture of acetonitrile and ether to give a racemic product as prisms; 0.39 g (9.7%); mp. 201–203° C.

EXAMPLE 2

S(−) 3-(2-Phenyl-2-hydroxyethyl)-4,5-dimethyl-thiazolium chloride:

S (−) 2-chloro-1-phenylethanol.

2-Chloroacetophenone (3 g., 19.4 mmole) was treated with (−) DIP-chloride (6.7 g., 20.9 mmole) in anhydrous THF (20 mL) at dry-ice bath temperature and left overnight. The temperature was raised to room temperature and THF was removed in vacuo. The residue was dissolved in ether (100 mL). The diethanolamine (4.58 g., 42.6 mmole) was added and the mixture stirred at room temperature for 5 hrs. The separated solid was filtered and the filtered cake was washed with hexane (40 mL) and ether (30 mL). The combined filtrates were to dryness to give 6.36 g of crude product. This was purified by silica gel column chromatography using 1% ether and petroleum ether 1.71 g (56%) of the desired product was obtained as an oil.

S (−) 3-(2-Phenyl-2-hydroxyethyl)-4,5-dimethylthiazolium chloride.

The neat mixture of S (−) 2-chloro-1-phenylethanol (2.78 g., 17.8 mmole) and 4,5-dimethylthiazole (2 g., 17.7 mmole) were heated with stirring at 135° C. for 25 hrs. It was cooled to room temperature and water (30 mL) was added to the reaction mixture with stirring. The solution was extracted with ether (30 mL). The ether extract was again extracted with water (30 mL). The combined water layer was evaporated to dryness and the residue was crystallized with a mixture of acetonitrile and methyl tert-butyl ether. Yield: 0.63 g. (7.7%); mp. 189–190° C.; $[\alpha]_D^{25}$ −51.765 (Water, c 1.7732).

EXAMPLE 3

R(−) 3-(2-Phenyl-2-hydroxyethyl)-4,5-dimethyl-thiazolium chloride:

R (−) 2-chloro-1-phenylethanol.

2-chloroacetophenone (6.25 g., 40.4 mmole) was treated with (−) DIP-chloride (18 g., 56.1 mmole) in anhydrous THF (40 mL) at dry-ice bath temperature and left overnight. The temperature was raised to room temperature and THF was removed in vacuo. The residue was dissolved in ether (210 mL). The diethanolamine (9 g., 85.6 mmole) was added and the mixture stirred at room temperature for 5 hrs. The separated solid was filtered and the filtered cake was washed with ether (150 mL). The combined filtrates were to dryness to give 15.53 g. of crude product. This was purified by silica gel column chromatography using 1% ether and petroleum ether 4.32 g (68%) of the desired product as an oil.

R (−) 3-(2-Phenyl-2-hydroxyethyl)-4,5-dimethylthiazolium chloride.

The neat mixture of R (−) 2-chloro-1-phenylethanol (4.32 g., 27.6 mmole) and 4,5-dimethylthiazole (3.12 g., 27.6 mmole) were heated with stirring at 135° C. for 25 hrs. It was cooled to room temperature and water (30 mL) was added to the reaction mixture with stirring. The solution was extracted with ether (30 mL). The ether extract was again extracted with water (30 mL). The combined water layer was evaporated to dryness and the residue was crystallized with a mixture of acetonitrile and methyl tert-butyl ether. Yield: 0.44 g. (5.4%); mp. 187–189° C.; $[\alpha]_D^{25}$ +52.009 (Water, c=1.7824).

EXAMPLE 4

3-[2-(2′, 3′ or 4′-monohydroxyphenyl)-2-oxoethyl]-4,5-dimethylthiazolium bromide.

2-Bromo-4′-hydroxyacetophenone.

Copper (II) bromide (6 g, 26.9 mmole) was suspended in ethyl acetate (50 mL) and 4′-hydroxyacetophenone (2 g, 14.7 mmole) dissolved in chloroform (20 mL) was added to the suspension. The reaction mixture was refluxed for 8 hrs. and filtered hot through celite pad. The filtrate was evaporated to dryness to give the desired crude brown colored compound (mp=115–118° C.; yield: 3.03 g, 96%). The NMR spectrum and TLC [silica gel, Hexanes:EtOAc (1:1, v/v)] was in agreement with the desired product. It was used as such in the next step of the reaction without further purification.

This method was used to prepare:

(i) 2-Bromo-2′-hydroxyacetophenone from 2′-hydroxyacetophenone and copper (II) bromide. Yield: 3.30 g. (95%; oil).

(ii) 2-Bromo-3′-hydroxyacetophenone from −3′-hydroxyacetophenone and copper (11) bromide. Yield: 3.20 g. (92%; oil).

3-[2-(4′-Hydroxyphenyl)-2-oxoethyl]-4,5-dimethylthiazolium bromide.

The neat mixture of 2-bromo-4′-hydroxyacetophenone (3 g, 15 mmole) and 4,5-dimethylthiazole (1.71 g, 15 mmole) was heated at 110° C. for 3 hrs. It was dissolved in acetonitrile (15 mL) and cooled to room temperature. Tert-Butyl methyl ether (5 mL) was added and the reaction mixture kept at room temperature overnight. The product crystallized was filtered, washed well with a mixture of acetonitrile and tert-butyl methyl ether (1:1, v/v) and dried. It was recrystallized from a mixture of acetonitrile, ethyl alcohol and tert-butyl methyl ether. Yield: 3.18 g (64%); mp. 245–247° C. (dec.).

This method was used to prepare:

(i) 3-[2-(2′-Hydroxyphenyl)-2-oxoethyl]-4,5-dimethylthiazolium bromide from 2-bromo-2′-hydroxyacetophenone and 4,5-dimethylthiazole. Yield: 2.05 g. (38%), mp=208–209° C.

(ii) 3-[2-(3′-Hydroxyphenyl)-2-oxoethyl]-4,5-dimethylthiazolium bromide from 2-bromo-3′-hydroxyacetophenone and 4,5-dimethylthiazole. Yield: 1.52 g. (47%), mp=235–237° C.

EXAMPLE 5

3-(2-Phenyl-2-oxoethyl)-4-methyl-5-(hydroxymethyl)-thiazolium chloride

Thioformamide.

To formamide (20 g, 443 mmoL) dissolved in anhydrous THF (100 mL) was added phosphorous pentasulfide ($P_2S_5$) (20 g, 45 mmoL) while maintaining the temperature at 30–35° C. The mixture was stirred overnight at room temperature, filtered and stripped of THF. The crude product was suspended in ethyl acetate (40 mL) and cooled at −78° C. overnight, filtered and dried in vacuo at room temperature to give thioformamide (10.6 g, 39%). See Rynbrandt, R. H., Nishizawa, E. E., Balogoyen, D. P., Mezdoza, A. K., Annis, K. A.; J. Med. Chem. (1981), 24, 1507–1510.

4-Methyl-5-(ethoxycarbonyl)-thiazole.

Thiofirmamide (7.5 g, 122.72 mmoL), ethyl 2-chloroacetoacetate (16.4 g, 99.52 mmoL) and magnesium carbonate (20 g, 237.22 mmoL) were taken dioxane (100 mL) and heated at 110°C. for 4 hrs. The reaction mixture was cooled to room temperature and filtered to remove magnesium carbonate. The solvent was evaporated to dryness and the residue was taken in ether (2 mL) and washed successively with 0.5 M NaOH solution (2 mL×2) and saturated brine solution (100 mL) and dried over $Na_2SO_4$. It was filtered and evaporated to give 4-methyl-5-(ethoxycarbonyl)-thiazole as an oil which was purified by silica gel column chromatography using hexanes:EtOAc (8:2, v/v) as a eluent; yield: 3.28 g (17%).

4-Methyl-5-(hydroxymethyl)-thiazole.

A 250-mL, three necked round-bottomed flask fitted with a 100-mL dropping funnel, a nitrogen-inlet tube, and a reflux condenser was added lithium aluminium hydride (1 g, 26.35 mmoL) and anhydrous ether (50 mL). To the dropping funnel was added 4-methyl-5-(ethoxycarbonyl)-thiazole (3 g, 17.34 mmoL) and anhydrous ether (25 mL). While the suspension of lithiun aluminium hydride was gently stirred under a nitrogen atmosphere, the solution of 4-methyl-5-(ethoxycarbonyl)-thiazole was added dropwise at a rate maintaining a gentle reflux. When the addition was complete, the mixture was heated at reflux for 4 hrs. After the mixture had returned to room temperature, anhydrous ether (100 mL) was added. The gray reaction mixture was hydrolyzed by addition, in small parts, of a sufficient amount of wet sodium sulfate. The reaction mixture was filtered through a sintered-glass funnel. The organic layer separated and dried over $Na_2SO_4$. It was filtered and evaporated to give desired compound as an oil; yield: 590 mg (26%).

3-(2-Phenyl-2-oxoethyl)-4-methyl-5-(hydroxymethyl)-thiazolium chloride.

The neat reaction of 4-methyl-5-(hydroxymethyl)-thiazole (590 mg, 4.57 mmoL) and 2-chloroacetophenone (710 mg, 4.59 mmoL) was heated at 110° C. The mixture solidified within 15 minutes. Acetonitrile (10 mL) was added and the mixture refluxed for another 3 hrs. It was cooled to room temperature and tert-butyl methyl ether (5 mL) was added and the reaction mixture was left overnight at room temperature. The product crystallized was filtered and washed well with a mixture of hexanes:EtOAc (1:1, v/v) and dried. It was recrystallized from a mixture of actonitrile/ethanol/tert-butyl methyl ether; yield 130 mg (10%); mp. 240–242° C. (dec.).

EXAMPLE 6

3-[2-(Disubstituted-dihydrooxyphenyl)-2-oxoethyl] -4,5-dimethylthiazolium bromide.

2-Bromo-2', 4'-dihydroxyacetophenone.

Copper (II) bromide (6 g, 26.9 mmole) was suspended in ethyl acetate (50 mL) and 2', 4'-dihyroxyacetophenone (2 g, 13.1 mmole) dissolved in chloroform (20 mL) was added to the suspension. The reaction mixture was refluxed for 8 hrs. and filtered hot through celite pad. The filtrate was evaporated to dryness to give crude oil (3.0 g, 96%). The NMR spectrum and TLC [silica gel, Hexanes:EtOAc (1:1, v/v)] was in agreement with the desired product. It was used as such in the next step of the reaction without further purification.

This method was used to prepare:
(i) 2-Bromo-3', 5'-dihydroxyacetophenone from 3', 5'-dihydroxyacetophenone and copper (II) bromide.
(ii) 2-Bromo-2', 5'-dihydroxyacetophenone from 2', 5'-dihydroxyacetophenone and copper (II) bromide. Yield: 2.99 g; 99%

3-[2-(2', 4'-Dihydroxyphenyl)-2-oxoethyl]-4,5-dimethylthiazolium bromide.

The neat mixture of 2-bromo-2', 4'-dihydroxyacetophenone (3 g, 13 mmole) and 4,5-dimethylthiazole (1.71 g, 13.3 mmole) was heated at 110° C. for 3 hrs. It was dissolved in acetonitrile (15 mL) and cooled to room temperature. Tert-Butyl methyl ether (5 mL) was added and the reaction mixture kept at room temperature overnight. The product crystallized was filtered, washed well with a mixture of acetonitrile and tert-butyl methyl ether (1:1, v/v) and dried. It was recrystallized form a mixture of methanol and a few drops of water. Yield: 2.5 g (50%); mp. 257–260° C. (dec.).

This method was used to prepare:
(i) 3-[2-(3', 5'-Dihydroxyphenyl)-2-oxoethyl]-4,5-dimethylthiazolium bromide in 55% yield from 2-bromo-3', 5'-dihydroxyacetophenone and 4,5-dimethylthiazole; mp. 257–258° C. Yield: 2.05 g (21%).
(ii) 3-[2-(2', 5'-Dihydroxyphenyl)-2-oxoethyl]-4,5-dimethylthiazolium bromide in 57% yield from 2-bromo-2', 5'-dihydroxyacetophenone and 4,5-dimethylthiazole; mp. 231–232° C. Yield: 4.03 g (52%).
(iii) 3-[2-(3', 4'-Dihydroxyphenyl)-2-oxoethyl]-4,5-dimethylthiazolium chloride in 60% yield from commercially available 2-chloro-3', 4'-dihydroxyacetophenone and 4,5-dimethylthiazole; mp. 260–263° C. (dec.); yield: 3.9 g (48%).

| Tablets | mg/tablet |
| --- | --- |
| Compound of Invention | 50 |
| Starch | 50 |
| Mannitol | 75 |
| Magnesium stearate | 2 |
| Stearic acid | 5 |

The compound, a portion of the starch and the lactose are combined and wet granulated with starch paste. The wet granulation is placed on trays and allowed to dry overnight at a temperature of 45° C. The dried granulation is comminuted to a particle size of approximately 20 mesh. Magnesium stearate, stearic acid and the balance of the starch are added and the entire mix blended prior to compression on a suitable tablet press. The tablets are compressed at a weight of 232 mg. using a ¹¹⁄₃₂" punch with a hardness of 4 kg. These tablets disintegrate within a half hour according to the method described in USP XVI.

| Lotion | mg/g |
| --- | --- |
| Compound of Invention | 1.0 |
| Ethyl alcohol | 400.0 |
| Polyethylene glycol 400 | 300.0 |
| Hydroxypropyl cellulose | 5.0 |
| Propylene glycol | to make 1.0 g |

| Oral Rinse | |
| --- | --- |
| Compound of Invention | 1.4% |
| Chlorhexidine gluconate | 0.12% |
| Ethanol | 11.6% |
| Sodium saccharin | 0.15% |
| FD&C Blue No. 1 | 0.001% |
| Peppermint Oil | 0.5% |
| Glycerine | 10.0% |
| Tween 60 | 0.3% |
| Water to | 100% |

| Toothpaste | |
| --- | --- |
| Compound of Invention | 5.5% |
| Sorbitol, 70% in water | 25% |
| Sodium saccharin | 0.15% |
| Sodium lauryl sulfate | 1.75% |
| Carbopol 934, 6% dispersion in | 15% |
| Oil of Spearmint | 1.0% |
| Sodium hydroxide, 50% in water | 45% |
| Dibasic calcium phosphate dihydrate | |
| Water to | 100% |

EXAMPLE 11
Cross-Linking Inhibition Assay

Inhibition of cross-linking is assayed as described in U.S. Pat. No. 5,853,703.

EXAMPLE 12

Cross-Link Breaking Assay

The breaking of cross-links is assayed as described in U.S. Pat. No. 5,853,703.

EXAMPLE 13

Measurement of IgG Crosslinked to Red Blood Cells

IgG crosslinked to red blood cells, and inhibition of such crosslinking in animals to which a compound of the invention has been administered are assayed as described in U.S. Pat. No. 5,853,703.

EXAMPLE 14

Effects on Collagen

The effects on collagen of administering to an animal a compound of the invention can be assessed as described in U.S. Pat. No. 5,853,703.

The meaning of "effective amount" will be recognized by clinicians but includes an amount effective to (1) reduce, ameliorate or eliminate one or more symptoms of the disease sought to be treated, (2) induce a pharmacological change relevant to treating the disease sought to be treated, or (3) prevent or lessen the frequency of occurrence of a disease. In certain embodiments, should the compound at issue have glucose lowering activity, the amount is preferably less than a glucose lowering effective amount.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods can be used and that it is intended that the invention can be practiced otherwise than as specifically described herein. Accordingly, this invention includes all modifications encompassed within the spirit and scope of the invention as defined by the claims that follow.

What is claimed:

1. A pharmaceutical composition for administration to an animal for (i) improving the elasticity or reducing wrinkles of the skin, treating (ii) diabetes or treating or preventing (iii) adverse sequelae of diabetes, (iv) kidney damage, (v) damage to blood vasculature, (vi) hypertension, (vii) retinopathy, (viii) damage to lens proteins, (ix) cataracts, (x) peripheral neuropathy, or (xi) osteoarthritis, the composition comprising one or more compounds of the following formula:

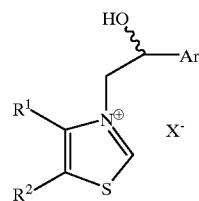

I wherein
$R^1$ and $R^2$ are independently hydrogen, hydroxy(lower)alkyl, lower acyloxy(lower)alkyl, or lower alkyl, or $R_1$ and $R_2$ together with their ring carbons form an aromatic fused ring;
Ar is an aryl group;
X is a pharmaceutically acceptable anion,
wherein each said fused aromatic ring or aryl group can be substituted with hydroxy groups and up to two groups selected from halo, loweralkoxy or di(loweralkyl)amino groups, or one or more alkyl, carboxy, carboxyalkyl, nitro or alkylenedioxy groups.

2. The composition of claim 1 wherein the compound is a 3-(2-phenyl-2-hydroxyethyl)-4,5-dimethyl-thiazolium salt.

3. The composition of claim 1 wherein the compound has 90% isomeric purity as the S(−) 3-(2-phenyl-2-hydroxyethyl)-4,5-dimethyl-thiazolium salt form.

4. The composition of claim 1 wherein the compound has 90% isomeric purity as the R(−) 3-(2-phenyl-2-hydroxyethyl)-4,5-dimethyl-thiazolium salt form.

5. The composition of claim 1 wherein at least one of $R^1$, $R^2$ or Ar is substituted with one or more hydroxy groups.

* * * * *